United States Patent [19]
Campbell et al.

[11] Patent Number: 5,330,523
[45] Date of Patent: Jul. 19, 1994

[54] IMPLANTABLE DEFIBRILLATOR PATCH LEAD

[75] Inventors: Arthur A. Campbell, Reseda; Stephen M. Jones, Canyon Country; Phong D. Doan, Stevenson Ranch, all of Calif.

[73] Assignee: Siemens Pacesetter, Inc., Sylmar, Calif.

[21] Appl. No.: 926,076

[22] Filed: Aug. 5, 1992

[51] Int. Cl.$^5$ .............................................. A61B 1/04
[52] U.S. Cl. ................................................... 607/129
[58] Field of Search ............... 128/784, 785, 798, 639, 128/640, 419 D, 639–642; 607/5, 152, 116, 119, 12, 129, 130–132

[56] References Cited

U.S. PATENT DOCUMENTS

| | | | |
|---|---|---|---|
| 1,212,541 | 1/1916 | Morse | 128/798 |
| 2,536,271 | 1/1951 | Fransen | 128/798 |
| 4,314,095 | 2/1982 | Moore et al. | 174/84 C |
| 4,411,277 | 10/1983 | Dickhudt | 128/784 |
| 4,827,932 | 5/1989 | Ideker et al. | 128/784 X |
| 5,042,463 | 8/1991 | Lekholm | 128/642 X |

OTHER PUBLICATIONS

Timmis, Gerald C., "The Electrobiology and Engineering of Pacemaker Leads," Chapter 4, pp. 35–90, Section—Electrical Therapy for Bradyarrhythmias, *Electrical Therapy for Cardiac Arrhythmias* (W. B. Saunders Company—1990).

*Primary Examiner*—Lee S. Cohen
*Assistant Examiner*—Jeffrey R. Jastrzab
*Attorney, Agent, or Firm*—Lisa P. Weinberg; Malcolm J. Romano

[57] ABSTRACT

A defibrillator patch lead having a connecting element interconnecting an electrical conductor and a wire mesh electrode pad. The connecting element includes a body portion which has a slot cut therein into which a portion of the wire mesh electrode is inserted and securely bonded, preferably by laser welding. The connecting element further includes a female connector portion which is designed to mate with a male core sleeve. The core sleeve includes a channel for receiving a first conductor therein, which is then electrically and mechanically connected (e.g., by either welding or crimping). The core sleeve also includes an orifice for receiving a second conductor, which is subsequently electrically and mechanically connected (e.g., by either welding or crimping) between the core sleeve and the connecting element. Advantageously, the combination of the core sleeve, two conductors, and the connecting element have superior pull strength over conventional methods of attachment. Furthermore, the use of two conductors provides additional redundancy in the event one conductor fails.

9 Claims, 2 Drawing Sheets

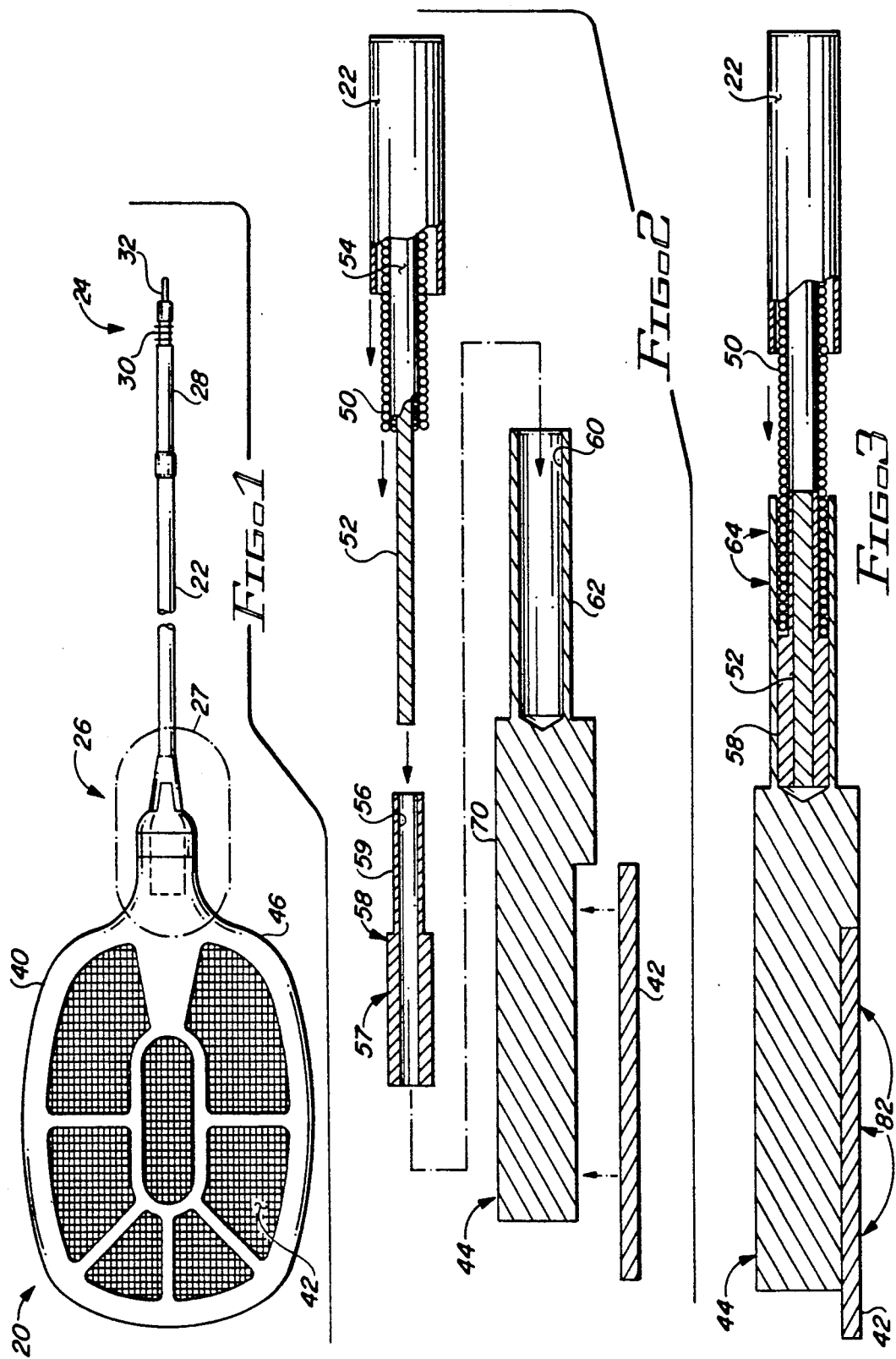

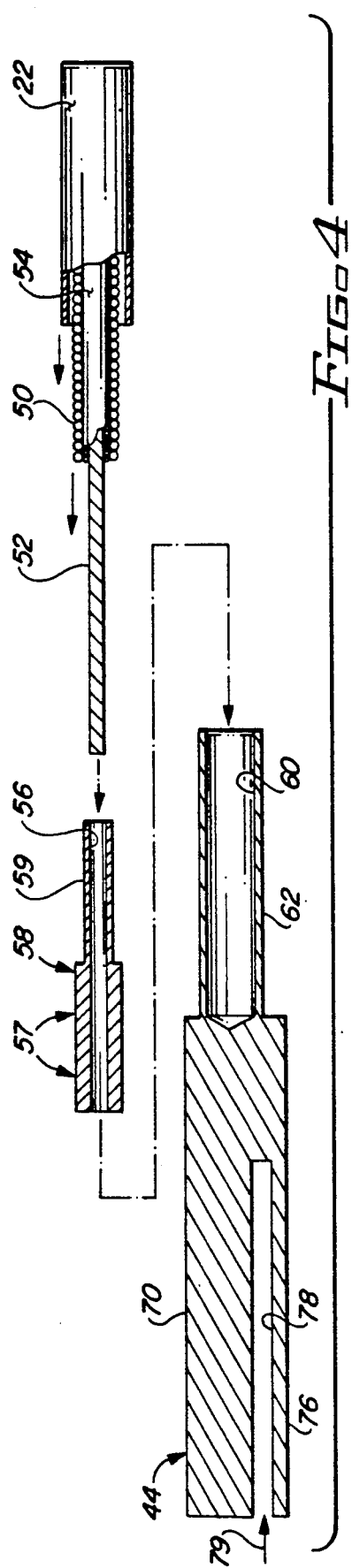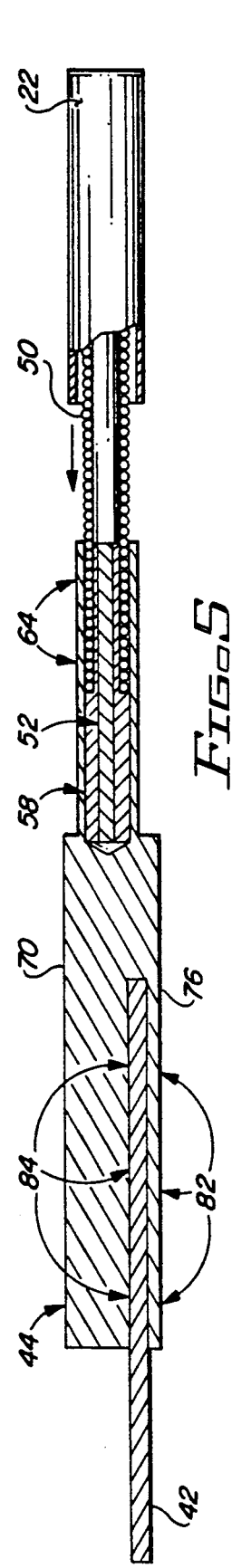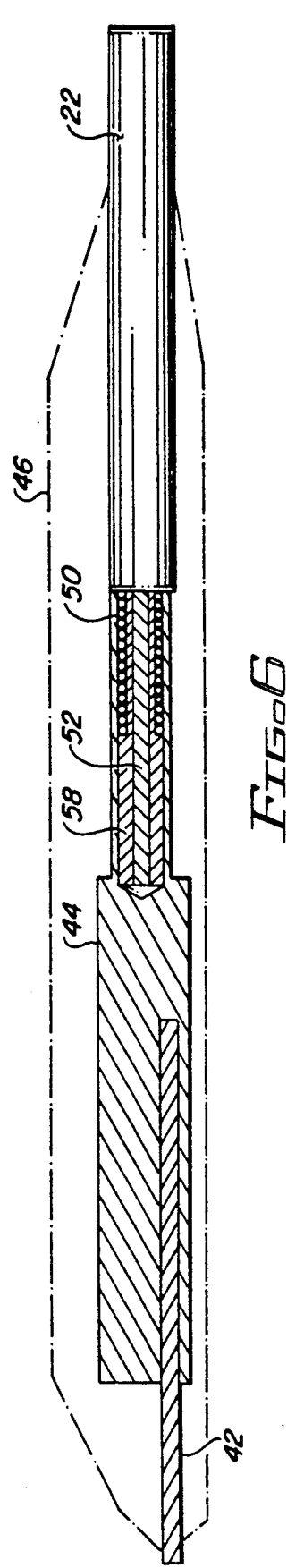

IMPLANTABLE DEFIBRILLATOR PATCH LEAD

FIELD OF THE INVENTION

The present invention relates to the field of implantable medical devices for sensing and manipulating cardiac activity. More specifically, the present invention details a defibrillator patch lead adapted to be affixed to the exterior surface of the heart and connected via a conductor to a signal processing and power generating unit.

BACKGROUND OF THE INVENTION

The continuing evolution in the medical field of the study and control of cardiac activity requires advances in the designs of implantable devices utilized to monitor and control the cardiac activity. Various types of electrodes are currently utilized which are either implanted into an interior chamber of the heart or affixed to the exterior surface of the heart. These devices, depending upon their intended locations, have associated specific design requirements. For the devices designed to be affixed to the exterior surface of the heart, the anatomical environment places design on both the materials and construction of the devices. For example, cardiac defibrillator patch leads preferably have a relatively large electrode surface area in order to allow delivery of a polarizing charge or pacing stimulation of sufficient magnitude.

For patch electrodes which are affixed to the external surface of the heart, the environment requires that the electrode be extremely resistant to fractures caused by the flexing resulting from the continuous beating of the heart. In addition, the electrodes must exhibit high conductivity and polarizing capacity, high flexibility, and biological inertness. For cardiac defibrillation electrodes, the use of extremely fine titanium or platinum wire mesh, which provides very good electrical properties while conforming to the shape of the heart, has become standard as the material for a defibrillator patch electrode.

Additionally, when using electrodes which are placed directly on the heart, it is a requirement that the electrical conductors interconnecting the patch electrode and a signal processing and power generating assembly be extremely flexible and resistant to fracture from repeated flexion. As may be appreciated, the heart undergoes continuous movement which cannot be inhibited by the conductors or the electrodes affixed to the surface of the heart. In recognition of the critical nature of the devices, any fracture or degradation in the performance of the electrode and/or the conductors is unacceptable.

Given the above constraints for both the defibrillator patch electrode and the associated electrical conductors, an optimum design may be a conductor which flares at one end into a mesh which may be affixed to the surface of the heart. However, this configuration would be difficult to manufacture, and it is often the case that the wire forming the electrode patch is of a different material from that of the conductor. Accordingly, some mechanism for affixing the electrode patch to the conductor is required. One such arrangement is depicted and described in U.S. Pat. No. 4,314,095 (Mirowski et al.). This patent utilizes a generally U-shaped sleeve which is affixed to the electrode mesh and which is designed to form a channel into which the flexible electrical conductors are inserted and crimped into place.

The various types of materials for the electrodes and conductors, as well as various specific design considerations influence the method of affixing the conductors to the wire mesh of the electrode patch. In this regard, it should be noted that the particular difficulty comes in providing secure electrical and mechanical contact between the electrical conductors and electrode mesh. This point of joinder is one of the more challenging aspects of the design of the defibrillator patch lead.

SUMMARY OF THE INVENTION

The present invention is directed to the design and construction of a defibrillator patch lead. More specifically, the present invention details a defibrillator patch lead having an electrical conductor which is inserted into a hollow cylindrical projection extending from a connecting element and then welded or crimped in place. The connecting element also includes a body portion which has a slot cut therein into which a portion of a titanium or platinum wire mesh element is inserted. The connecting element then undergoes a laser welding operation to secure the titanium or platinum wire mesh in the slot of the connecting element such that the connecting element is securely bonded to the mesh. The connecting element is specifically designed and configured such that the laser welding will not result in burn-through. Thereby, the resultant interconnection of the electrode patch with the electrical conductor is secure yet compliant, in accordance with the flexure requirements of the intended case.

Another feature of the connecting element lies in the method of attaching the conductor to the connecting element. The connecting element includes a female connector portion which is designed to mate with a male core sleeve. The core sleeve includes a channel for receiving a first conductor therein, which first conductor is then electrically and mechanically connected thereto by either welding or crimping. The core sleeve also includes means for receiving a second conductor, which second conductor is subsequently electrically and mechanically connected thereto (e.g., by either welding or crimping) between the core sleeve and the connecting element. Advantageously, the combination of the core sleeve, two conductors and the connecting element have superior pull strength over conventional methods of attachment. Furthermore the use of two conductors provides additional redundancy in the event one conductor fail.

BRIEF DESCRIPTION OF THE DRAWINGS

FIG. 1 illustrates a defibrillator patch lead according to the present invention;

FIG. 2 is an exploded cross-sectional view of one embodiment for the interconnecting element which affixes the electrical conductor to the electrode mesh of the defibrillator patch lead;

FIG. 3 is a cross-sectional view of the assembled patch electrode shown in FIG. 2;

FIG. 4 depicts an exploded cross-sectional view of the preferred embodiment of the connecting element according to the present invention;

FIG. 5 is a cross-sectional view of the assembled patch electrode shown of the preferred embodiment shown in FIG. 4; and FIG. 6 depicts a cross-sectional view illustrating the assembled connecting element of the present invention.

DETAILED DESCRIPTION OF THE PREFERRED EMBODIMENT

FIG. 1 illustrates a defibrillator patch lead 20 according to the present invention. The patch lead 20 includes an elongated lead body 22 extending from a proximal end 24 to a distal end 26. The proximal end 24 includes a connector assembly 28 having a biocompatible material formed to provide sealing rings 30, and to leave exposed an electrical conductor pin 32. The connector assembly 28 is configured for insertion into a receiving element of a signal processing and power generating assembly (not shown).

At the distal end 26 of the defibrillator patch lead 20 is located an electrode assembly 40. The electrode assembly 40 includes a wire mesh element 42 which is secured via a conductive connector element 44, shown in phantom lines, to the electrical conductors within the elongated lead body 22. The connector element 44 as well as the peripheral edge of the wire mesh element 42 are encased in a molded element 46, which is a biocompatible inert insulation material. The wire mesh element 42 may simply be a round- or oval-shaped wire mesh preferably formed from 17 to 19 gage (0.003–0.005 inch diameter) titanium or platinum wire, The portion of the patch lead 20 of FIG. 1, which is enclosed within the circle 27, is illustrated in greater detail in the cross-sectional views of FIGS. 2-6. FIGS. 2 and 3 illustrate one embodiment of the connector element 44 of the present invention. However, the preferred embodiment is illustrated in FIGS. 3 and 4. FIGS. 2-6 all include a number of common elements which are assigned the same number throughout FIGS. 1-6.

Starting at the right side of FIG. 2, the portion of the elongated lead body 22 is depicted as including an outer electrical conductor 50 which is wrapped about an insulator 54 which encases an inner electrical conductor 52. The inner electrical conductor 52 is stripped of the insulator 54, slidably inserted into a channel 56 of a conductive core sleeve 58, and crimped thereto at locations 57. The outer electrical conductor 50 is then slid over a protruding portion 59 of the core sleeve 58. The core sleeve 58 is configured to be inserted into a cylindrical cavity 60 defined by a conductive cylindrical element 62 projecting from the connector element 44. Upon insertion of the core sleeve 58 into the Cylindrical element 62, the core sleeve 58 and the outer conductor 50 are electrically and mechanically secured within the cylindrical element 62 by crimping or by laser welding at locations 64 (FIG. 3). The combination of the core sleeve 58, the two conductors (i.e., the inner and outer conductors 50 and 52), and the connector element 44 has approximately four times the pull strength over conventional methods of attachment. Furthermore, the use of two conductors provides redundancy should one conductor fail.

The connector element 44 also includes a body portion 70 which is preferably formed from titanium or platinum depending on the material for a wire mesh element 42. The connector element 44, as shown in FIG. 2, includes a recessed area 72 into which the wire mesh 42 is placed and subsequently laser welded to the body portion 70 of connector element 44 at locations 82 (FIG. 3).

The preferred method of welding the wire mesh element 42 to the body portion 72 is illustrated in FIGS. 4 and 5. In FIG. 4, the body portion 70 of connector element 44 includes a cantilevered retaining flap 76, which defines a slot opening 78 against the body 70. The wire mesh element 42 (shown in FIG. 5) is inserted into the slot opening 78 in the direction of the arrow 79 and secured via a laser welder to the connector element 44 at weld points 82 (FIG. 5). Preferably, the width of the slot 78 is closely matched to the thickness of the wire mesh element 42. Thus, the thickness of the slot opening 78 is preferably in the range of about 0.25 mm to 0.30 mm.

The connector element 44 is preferably fabricated from titanium or platinum to provide high corrosion resistance and durability. In addition, the wire mesh element 42 is preferably fabricated from titanium (which may have a titanium nitride surface coating) or from platinum.

In order to optimize the mechanical and electrical bond between the connector element 44 and wire mesh element 42, the thickness of the retaining flap 76 must be matched with the laser energy. Thus, for a titanium or platinum connector element 44, the retaining flap 76 will have a thickness in the range of between about 0.2 mm and 0.7 mm for a 3.25 joule laser and 3 millisecond period.

The assembled connector element 44 and portions of the elongated lead body 22 and wire mesh element 42 are illustrated in the cross-sectional view of FIG. 5. At the laser weld points 82 the material of the retaining flap 76 melts and rehardens, securing the retaining flap 76 to the wire mesh element 42 which is inserted into the slot opening 78. In addition, the material of the wire mesh element 42 melts to the body portion 70 of the connector element 44 at locations 84, such that the metal of the body 70 is secured to the wire mesh element 42. With this construction, the mechanical and electrical connection from the conductors through the connecting element 44 and to the wire mesh element 42 is significantly enhanced and will survive the repeated flexure accompanying its intended location on the exterior surface of the heart.

It should also be noted that substantially all of the connector element 44 and portions of the wire mesh element 42 as well as portions of the elongated lead body 22 will be encased in the biocompatible material of the molded element 46, to prevent corrosion and to minimize the foreign body reaction to the patch lead 20. The encasing material of the molded element 46 is shown by the dashed lines in FIG. 6.

As may now be appreciated, the present invention teaches a method of attaching a wire mesh patch electrode to an electrical conductor to form an implantable defibrillator patch lead. The method is accomplished by providing a conductive connecting element having a body portion and a projecting cylindrical portion for receiving and securely retaining one end of an electrical conductor, forming a receiving slot in the body portion of the connecting element, inserting a portion of the wire mesh patch electrode in the receiving slot, and directing a laser beam at the connecting element to laser weld the wire mesh patch electrode in the receiving slot of the connector element.

The method further contemplates providing a coaxial conductor having an inner and an outer conductor, and affixing a core sleeve about the end of the coaxial conductor prior to insertion into the projecting cylindrical portion of the connector element. The method of attaching the core sleeve to the connector element comprises the steps of slidably inserting the inner conductor into a channel within the core sleeve and sliding the outer conductor over a narrow protruding portion of the core sleeve. Preferably, laser welding or crimping is performed between the inner conductor and the main body of the core sleeve. The core sleeve is then slidably inserted within the projecting cylindrical portion of the connector portion. The outer conductor is then crimped (or otherwise electrically connected) between the connector portion of the connector element and the protruding portion of the core sleeve.

Preferably, the method further contemplates forming the connecting element and the wire mesh patch electrode from titanium or platinum. Alternative and/or additional steps may include: coating the wire mesh electrode with titanium nitride; forming the wire mesh patch electrode from 17 to 19 gage wire; and affixing a sleeve about the end of the electrical conductor prior to insertion into the projecting cylindrical portion of the connector element.

It should be evident from the foregoing description that the present invention provides many advantages over defibrillator patch leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable patch lead for use with an implantable defibrillation device, comprising:
   an electrical conductor having a proximal end and a distal end;
   a proximal connector, coupled to the proximal end of the electrical conductor, for electrically connecting the conductor to the implantable defibrillation device;
   a wire mesh patch electrode;
   an electrically conductive connector element having a body portion defining a slot into which a portion of the wire mesh patch electrode is inserted and bonded, the electrically conductive connector element also having receiving means, spaced from said slot, for receiving and securely retaining the electrical conductor, the electrically conductive connector element thereby electrically interconnecting the electrical conductor and the wire mesh patch electrode; and
   means for electrically, insulating the electrical conductor, the electrically conductive connector element, and a peripheral portion of the wire mesh patch electrode in a biocompatible insulation material.

2. The implantable patch lead of claim 1, wherein the electrical conductor comprises a coaxial conductor having an inner conductor and an outer conductor with insulation means therebetween for electrically insulating the inner conductor from the outer conductor, further comprising:
   a core sleeve having a main body, a narrow protruding portion, and a channel therethrough, the channel being for slidably inserting and electrically connecting the inner conductor therein, the narrow protruding portion being for sliding the outer conductor thereover and electrically connecting thereto, the core sleeve being slidably inserted within the receiving means of the connector element and electrically connected thereto.

3. The implantable patch lead of claim 1, wherein the wire mesh patch electrode is bonded in the slot of the connector element by a laser weld.

4. The implantable patch lead of claim 3, wherein the wire mesh patch electrode is formed from a material selected from the group consisting of titanium and platinum wire.

5. The implantable patch lead of claim 4, wherein the wire mesh patch electrode is formed from 17 to 19 gage wire.

6. An implantable patch lead for use with an implantable defibrillation device, comprising:
   a coaxial conductor having an inner and an outer conductor and having a proximal end and body end;
   a proximal connector, coupled to the proximal end of the coaxial conductor, for electrically connecting the coaxial conductor to the implantable defibrillation device;
   a wire mesh patch electrode;
   an electrically conductive connector element having a body portion and a connector portion, the body portion having means for mechanically and electrically connecting the wire mesh patch electrode thereto, the connector portion having a cavity therein;
   a core sleeve having a main body, a narrow protruding portion, and a channel therethrough, the channel being for slidably inserting and electrically connecting the inner conductor of the coaxial conductor therein, the narrow protruding portion being for sliding the outer conductor of the coaxial conductor thereover and electrically connecting thereto, the core sleeve being slidably inserted within the cavity of the connector portion and electrically connected thereto; and
   means for electrically insulating the inner and outer conductors of the coaxial conductor, the electrically conductive connector element and a peripheral portion of the wire mesh patch electrode in a biocompatible insulation material.

7. The implantable defibrillator patch lead of claim 6, wherein:
   the inner conductor is crimped to the main body of the core sleeve; and
   the outer conductor is crimped between the electrically conductive connector element and the core sleeve.

8. The implantable patch lead of claim 6, wherein the body portion of the electrically conductive connector element includes a slot into which a portion of the wire mesh patch electrode is inserted and bonded.

9. An implantable defibrillator patch lead for use with an implantable defibrillation device comprising:
   a coaxial conductor having a proximal end and a distal end;
   a proximal connector, coupled to the proximal end of the coaxial conductor, for electrically connecting the coaxial conductor to the implantable defibrillation device;
   a wire mesh patch electrode; and
   a connector element having a body portion forming an electrical interconnection between the patch electrode and the coaxial conductor, the body portion defining a slot into which a portion of the wire mesh patch electrode is inserted and bonded by laser welding, and a hollow cylindrical projection extending from the body portion of the connector element to receive and securely retain one end of the coaxial conductor at a location spaced from the slot into which said wire mesh patch electrode is bonded.

* * * * *

UNITED STATES PATENT AND TRADEMARK OFFICE
CERTIFICATE OF CORRECTION

PATENT NO. : 5,330,523
DATED : July 19, 1994
INVENTOR(S) : Arthur A. Campbell et al.

It is certified that error appears in the above-indentified patent and that said Letters Patent is hereby corrected as shown below:

In col. 6, line 13, delete "body" and insert therefor --distal--.

Signed and Sealed this

Twenty-third Day of May, 1995

Attest:

BRUCE LEHMAN

*Attesting Officer*  *Commissioner of Patents and Trademarks*